(12) United States Patent
Intelisano (10) Patent No.: US 7,584,785 B2
(45) Date of Patent: Sep. 8, 2009

(54) GROUNDWATER SAMPLING DEVICE

(75) Inventor: Craig Intelisano, Bradenton, FL (US)

(73) Assignee: Concurrent Technologies International, LLC, Bradenton, FL (US)

( * ) Notice: Subject to any disclaimer, the term of this patent is extended or adjusted under 35 U.S.C. 154(b) by 0 days.

(21) Appl. No.: 11/882,755

(22) Filed: Aug. 3, 2007

(65) Prior Publication Data

US 2008/0087413 A1    Apr. 17, 2008

Related U.S. Application Data

(62) Division of application No. 11/060,168, filed on Feb. 17, 2005, now Pat. No. 7,525,141.

(51) Int. Cl.
*E21B 43/00* (2006.01)
*F04B 17/03* (2006.01)

(52) U.S. Cl. .................. 166/69; 166/105; 166/66.4; 166/264; 417/423.15

(58) Field of Classification Search .......... 166/69, 166/105, 66.4, 264; 417/423.3, 423.15, 422; 310/87; 73/864.34
See application file for complete search history.

(56) References Cited

U.S. PATENT DOCUMENTS

| | | | |
|---|---|---|---|
| 938,878 A | 11/1909 | Larkin | |
| 2,218,003 A * | 10/1940 | Hawley, Jr. .................. 310/87 |
| 2,320,708 A * | 6/1943 | Yost ...................... 417/423.11 |
| 2,450,137 A * | 9/1948 | Harlamoff .................. 417/350 |
| 2,506,827 A | 5/1950 | Goodner | |
| 2,627,816 A * | 2/1953 | Kaatz et al. .................. 417/422 |
| 2,662,206 A * | 12/1953 | Schaefer ...................... 318/482 |
| 3,041,977 A * | 7/1962 | Boyd ........................ 417/414 |
| 3,126,831 A * | 3/1964 | Deters ........................ 417/359 |
| 3,135,212 A * | 6/1964 | Todd et al. ............... 417/423.1 |
| 3,294,993 A | 12/1966 | Komor et al. | |
| 3,371,613 A | 3/1968 | Dahlgren et al. | |
| 3,719,429 A * | 3/1973 | Rule .......................... 415/201 |
| 3,764,236 A * | 10/1973 | Carter ........................ 417/372 |
| 3,850,550 A | 11/1974 | Kaessen | |
| 4,890,988 A | 1/1990 | Kramer et al. | |
| 4,928,771 A | 5/1990 | Vandevier | |
| 4,961,018 A * | 10/1990 | Akhter ........................ 310/87 |
| 5,220,829 A | 6/1993 | Manke et al. | |
| 5,238,060 A | 8/1993 | Neihaus et al. | |
| 5,250,863 A | 10/1993 | Brandt | |
| 5,293,931 A | 3/1994 | Nochols et al. | |
| 5,297,943 A | 3/1994 | Martin | |
| RE34,754 E | 10/1994 | Dickinson et al. | |
| 5,616,973 A | 4/1997 | Khazanov et al. | |
| 5,648,694 A | 7/1997 | Kobayashi et al. | |

(Continued)

OTHER PUBLICATIONS

Notice of Assingnment of Reexamination Request dated Aug. 15, 2007 and Office Action dated Oct. 3, 2007.

(Continued)

*Primary Examiner*—Kenneth Thompson
(74) *Attorney, Agent, or Firm*—Novak Druce & Quigg LLP (57) ABSTRACT

A replaceable DC electric motor and kit for a groundwater sampling and pumping device and system for withdrawing groundwater from a well. The motor is provided with means to align the motor with an alignment pin in the groundwater sampling device.

11 Claims, 6 Drawing Sheets

U.S. PATENT DOCUMENTS

| | | |
|---|---|---|
| 5,684,346 A | 11/1997 | Mickos et al. |
| 5,708,220 A | 1/1998 | Burge |
| 5,997,262 A * | 12/1999 | Finkbeiner et al. ........ 417/410.4 |
| 6,028,386 A * | 2/2000 | Kech et al. ................... 310/194 |
| 6,121,698 A | 9/2000 | Sexton |
| 6,158,509 A | 12/2000 | Peterson |
| 6,691,782 B2 | 2/2004 | Vandevier |
| 6,758,273 B2 | 6/2004 | Learned |
| 6,890,160 B2 * | 5/2005 | Dokas ..................... 417/423.3 |

OTHER PUBLICATIONS

Request for Ex Parte Reexamination Under 35 U.S.C. §§302-307 filed Aug. 9, 2007.

* cited by examiner

GROUNDWATER SAMPLING DEVICE

CROSS-REFERENCE TO RELATED APPLICATIONS

This application is a divisional application of U.S. application Ser. No. 11/060,168, filed on Feb. 17, 2005, now U.S. Pat. No. 7,525,141 B2.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to systems and methods for gathering liquid samples using a submersible pump placed into a pre-established well for analysis and/or groundwater removal and groundwater remediation and circulation of fluids, and more particularly to a device and system for these purposes which includes an easily replaceable motor and a unique water flow passage structure and internal sealed electrical contacts which both prolong motor life and facilitate replacement thereof.

2. Description of Related Art

The taking of groundwater samples from a pre-established well for the purpose of groundwater sampling and/or removal is well known. These samples are typically taken by a submersible pump device which is descended into the well as supported and controlled by electrical power conduits and a flexible fluid conduit for conveying groundwater up to the ground surface by the pump device for removal or analysis.

A number of prior art devices are known to applicant which are disclosed in the following U.S. Patents:

U.S. Pat. No. 5,238,060 to Niehaus, et al.
U.S. Pat. No. 6,158,509 to Peterson
U.S. Pat. No. 5,708,220 to Burge
U.S. Pat. Re. No. 34,754 to Dickinson, et al.
U.S. Pat. No. 5,220,829 to Manke, et al.
U.S. Pat. No. 6,758,273 to Learned U.S. Pat. No. 5,238,060 to Niehaus discloses a fluid sampling apparatus for withdrawing samples of groundwater or other fluids. The pump includes a packer associated therewith which minimizes the amount of liquid which must be pumped to purge the well prior to obtaining an acceptable sample.

A method and apparatus for gathering liquid samples using a submersible pump is further disclosed by Peterson in U.S. Pat. No. 6,158,509. The submersible pump is operated by means of a surface valving system and solenoid systems mounted on the submersible pump. U.S. Pat. No. 5,708,220 to Burge teaches a liquid sampling device comprising a submersible liquid sampling device and a ground level sample receiving and control facility.

Dickinson, et al., in U.S. Pat. Re. No. 34,754 discloses a fluid sampling apparatus for withdrawing samples of groundwater or other fluids from a well or other monitoring site, said apparatus comprising a pump means, conduit means and a wellhead assembly. U.S. Pat. No. 5,220,829 to Manke, et al. teaches a downhole formation test pump including a progressive cavity pump and Learned discloses methods, apparatus and a low-flow groundwater sampling system in U.S. Pat. No. 6,758,273.

The present invention provides such a groundwater sampling device and system for withdrawing groundwater from a pre-established well which device is readily serviceable by the quick and convenient removal and replacement of the motor contained therein and for heightened flow and cooling characteristics around the motor for extended life.

BRIEF SUMMARY OF THE INVENTION

This invention is directed to a groundwater sampling and pumping device and system for withdrawing groundwater from a well. The device includes a hollow outer housing having water inlet ports formed through a bottom thereof and a hollow inner housing sized to be positioned coaxially within the outer housing and defining a water flow passage therebetween, the respective bottoms being spaced to define a lower portion of the water passage whereby water ports are in fluid communication with the water passage. An electric motor in the inner housing is connected to a water impeller operably positioned between the bottoms to draw groundwater into the water passage. A motor module cap establishes sealed connection to the electrical conduit passing longitudinally to the electrical input terminals of the motor while an output cap is sealingly removably engaged to the open end of the outer housing and includes an aperture for sealingly passing the electrical conduit longitudinally therethrough and a water outlet port for discharging water from the well upwardly therefrom. The water passing upwardly through the water flow passage provides cooling for the motor.

It is therefore an object of this invention to provide a groundwater sampling device for withdrawing groundwater from a pre-established well which is highly serviceable by the quick and easy replacement of the sealed internal electric motor contained therein.

Still another object of this invention is to provide a very high quality and high capacity groundwater sampling device and system for withdrawing groundwater from a pre-established well and which includes a jacket or water passage for water flow around the motor for heightened cooling and increased motor longevity.

Yet another object of this invention is to provide a groundwater sampling device for pumping groundwater from a pre-existing well which is readily serviceable and includes convenient sealed internal electrical contact components which facilitate servicing and replacement of the internal sealed motor by providing automatic electrical contact between the electrical conduit and the motor contacts.

In accordance with these and other objects which will become apparent hereinafter, the instant invention will now be described with reference to the accompanying drawings.

DETAILED DESCRIPTION OF THE INVENTION

Figure 1:
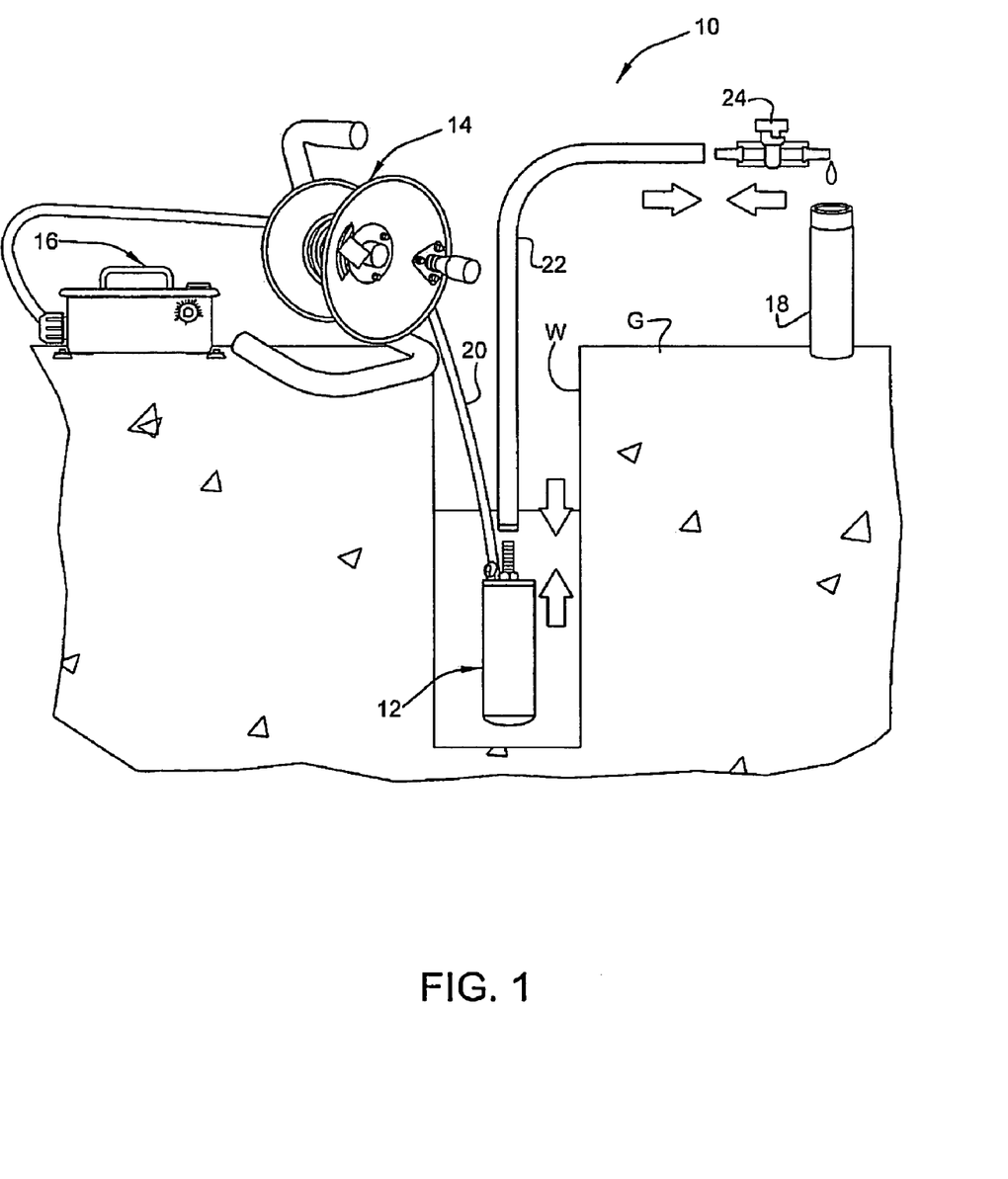
FIG. 1 is a simplified pictorial view of the system of the invention.
Figure 2:
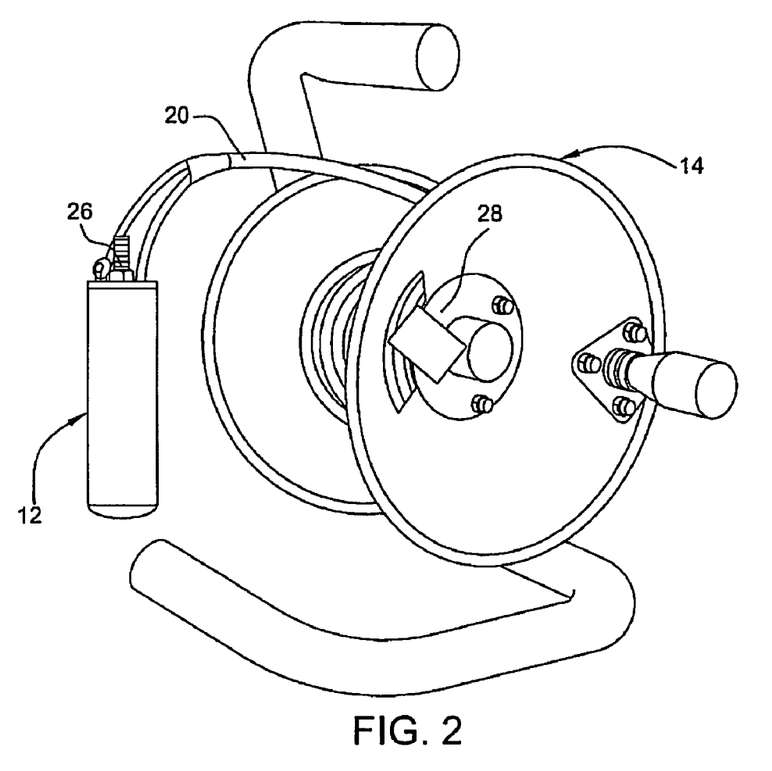
FIG. 2 is a perspective view of the preferred embodiment of the groundwater sampling device and associated aboveground electrical conduit reel apparatus.
Figure 3:
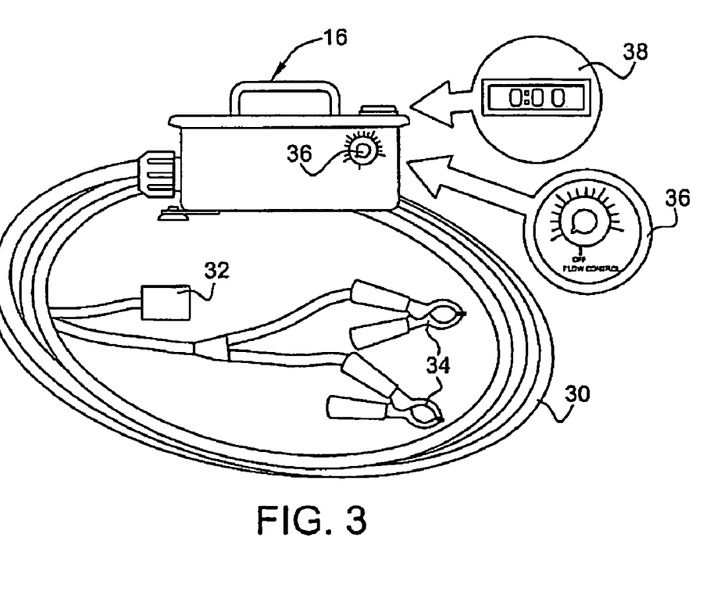
FIG. 3 is a perspective view of the power booster/controller of the system.

Referring now to the drawings, and firstly to FIGS. 1, 2 and 3, the system is there shown in FIG. 1 generally at numeral 10 and includes a water sampling device 12 in the form of a submersible groundwater pump, an electrical conduit reel apparatus 14 which interconnects a voltage controller/booster device 16 to the device 12 and further includes a sample vial 18 into which the groundwater is pumped out of a pre-established well W through a water conduit 22 for collection.

The device 12 is described in more detail herebelow and is positionable within the well W formed into the ground below grade level G. The depth of the device 12 is controlled primarily by the feeding of the electrical conduit 20 from the reel apparatus 14. The system voltage/current controller/booster 16 includes a connection to the electrical conduit 20 through attachment of fitting 32 to the mating fitting 28 connected to the reel apparatus 14. Electrical contacts 34, which are attachable to the terminals of a low voltage d.c. electrical power source such as a 12-volt battery, provide the power input into the controller 16. By the adjustment of the variable voltage adjuster 36 which is monitored by the liquid crystal display at 38, voltage output from the controller 16 into the motor contained within the device 12 is thereby provided.

The controller 16 inputs direct current from the 12-volt battery and produces an output voltage to run the device 12 with the specified parameters. The controller 16 boosts the voltage to a fixed 30 volts and then, using a buck converter, puts out a selected fixed voltage to the pump to operate the device 12 at the selected parameters. Consideration is given to the effective wire loss to maximize water output or pressure head that can be pumped.

Still referring to FIG. 1, when the sampling device 12 is activated, groundwater is forced upwardly through flexible conduit 22, through a disposable valve 24 for dispersion of a controlled volume of groundwater into a VOA vial 18. Alternately, the system 10 may also be used to simply evacuate groundwater from a pre-established well W, in which case the upper end of the flexible conduit 22 is directed to discharge the groundwater into a suitable container, above ground basin or the like.

The system 10 described herein is currently available commercially through Proactive Environmental Products of Bradenton, Fla. Two groundwater sampling devices 12 are generally available, the first under the trademark SS-MEGA-TYPHOON pump providing groundwater sampling and purging to a depth of 80' and the SS-MONSOON model providing a pumping depth to 120'. The pumping depth and performance in gallons per minute for each of these two sampling devices are shown herebelow:

| SS-MEGA-TYPHOON PUMP CHART | | | | | | | | | | |
|---|---|---|---|---|---|---|---|---|---|---|
| | Pumping Depth in Feet | | | | | | | | | |
| | 3 | 10 | 20 | 30 | 40 | 50 | 60 | 70 | 80 | 90 |
| Gallons Per Minute | 3.5 | 3.0 | 2.75 | 2.55 | 2.00 | 1.25 | 1.00 | .50 | .25 | N/A |

| SS-MONSOON PUMP CHART | | | | | | | | | | | | | |
|---|---|---|---|---|---|---|---|---|---|---|---|---|---|
| | Pumping Depth in Feet | | | | | | | | | | | | |
| | 3 | 10 | 20 | 30 | 40 | 50 | 60 | 70 | 80 | 90 | 100 | 110 | 120 | 130 |
| Gallons Per Minute | 4.0 | 3.75 | 3.5 | 3.25 | 3.0 | 2.75 | 2.0 | 1.75 | 1.5 | 1.25 | 1.0 | .50 | .25 | N/A |

Figure 4:
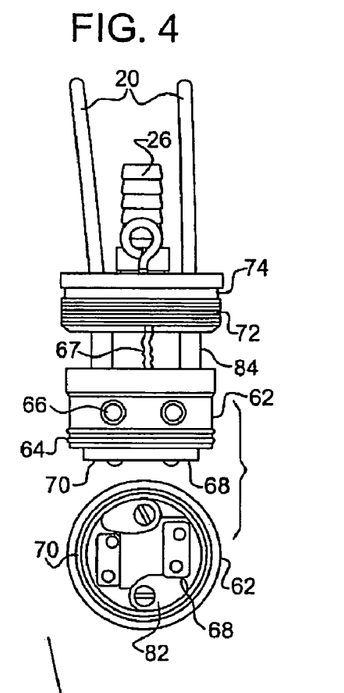
FIGS. 4, 5 and 6 are collectively an exploded view of the components of the groundwater sampling device 12.
Figure 5:
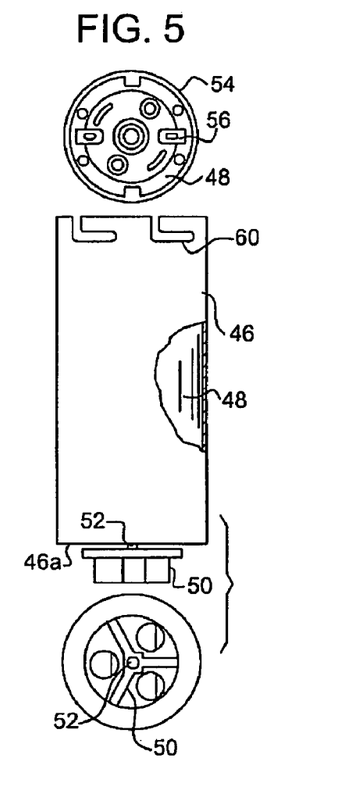
Figure 6:
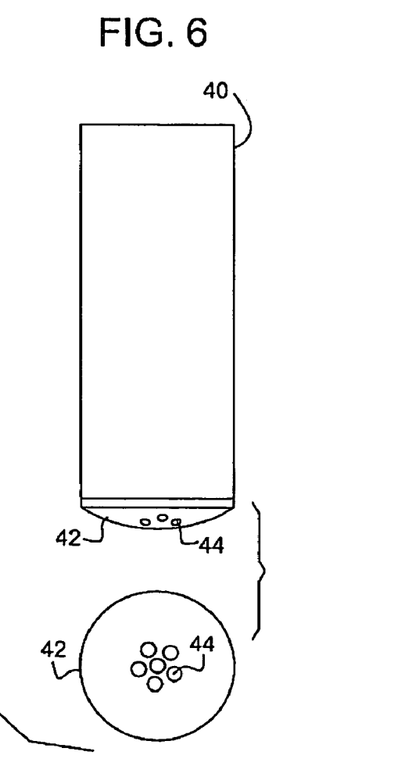

Referring now to FIGS. 4 to 7, the preferred groundwater sampling device 12, as best seen collectively in FIGS. 4, 5 and 6, may be viewed and best understood in three separate component stages, most of which are generally formed and/or machined of substantially non-corrosive material, such as TEFLON and stainless steel for strength. As seen in FIG. 6 in which both side and bottom views are shown, an outer cylindrical housing 40 formed of thin wall stainless tubular material hollow on the interior thereof, includes a machined bottom 42 threadably engaged into the tubular material which is formed as a segmented sphere having water inlet ports 44 formed centrally therethrough as also best shown in FIG. 7. These inlet ports 44 lead to an interior chamber 86 into which groundwater is drawn in the direction of arrows A in FIG. 7.

Figure 7:
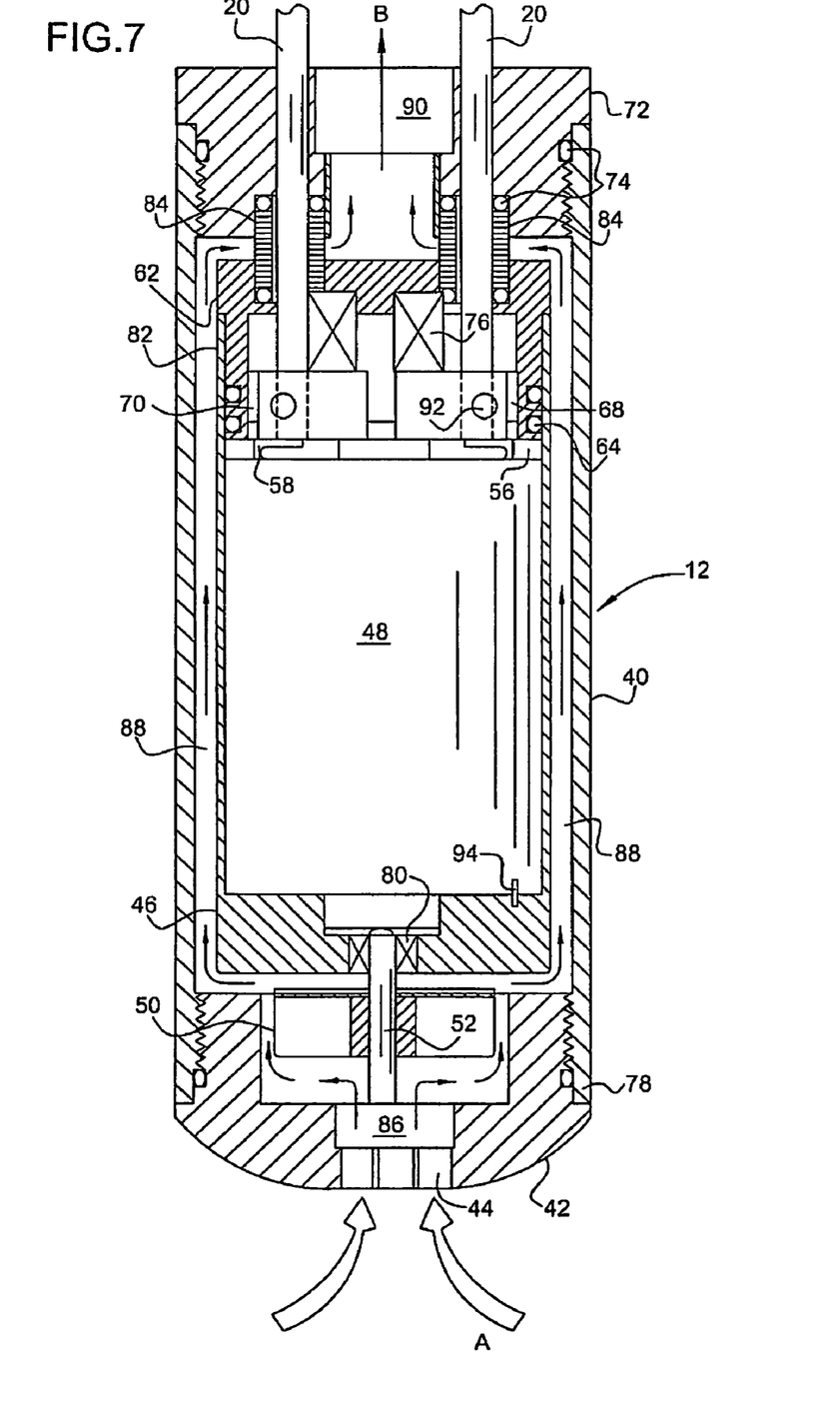
FIG. 7 is a cross section view of the groundwater sampling device 12 of FIGS. 4, 5 and 6.

In FIG. 5, showing side, top and bottom views, the inner hollow cylindrical tubular housing 46, also formed of thin wall stainless tubular material, includes a bottom 46 having a water seal 80 centrally disposed having an axial passageway to receive an output shaft 52 of a d.c. motor 48 sealingly fit there through upon motor 48 insertion into the inner housing 46. A water impeller 50 is attached to the output shaft 52 and is positioned as best seen in FIG. 7 within the interior chamber 86. A clearance gap is established by diameter selection between the inner diameter of the outer housing 40 and the outer diameter of the inner housing 48 to define a water passage or jacket 88 which upwardly receives groundwater in the direction of the arrows caused to flow into the inlet ports 44 in the direction of arrow A, continuing through the interior chamber 86, again in the direction of the arrows into the water passage 88.

The upper end of the motor 48 includes two electrical contacts 56 and 58 which receive electrical d.c. current and voltage from the controller 16 through the electrical conduit 20 as will be described in more detail herebelow. The preferred motor operating parameters for the SS-MEGA-TYPHOON model is 12.6 a/16.4 v.d.c. The SS-MONSOON model operates at 12.6 a/17.4 v.d.c.

Referring to FIG. 4, showing side and bottom views, the upper portion of the device includes a motor module cap 62 and an output cap 72. The output cap 72 is threadably engaged as best seen in FIG. 7 into the mating threads formed into the upper end of the outer housing 40. The motor module cap 62, also formed of machined material, includes outwardly extending pins 66 which, as best seen in FIG. 5, lockably engage into L-shaped slots 60 formed into the upper end of the inner housing 46 as shown. Following axial movement together with the pins 66 properly aligned with the longitudinal portion of these L-shaped slots 60, a simple twisting action seals and locks the motor module cap 62 into engagement with the upper end of the inner housing 46, O-rings 64 establishing the water-tight seal. Note importantly that alignment pin 94, anchored into bottom 46a, establishes proper rotational alignment between the motor 48 and the inner housing 46.

The output cap 72 and the motor module cap 62 are held together in fixed spaced .relationship by a plurality of longitudinally extending threaded fasteners 67. To maintain the spacing shown between these two components and, as best seen in FIG. 7 to establish the upper portion of the water passage 88, cylindrical sleeves 84 which are sealingly engaged at O-rings 74 at either end thereof, are fitted into mating aligned cavities formed into the facing surfaces of the output cap 72 and the motor module cap 62. These tubular spacers 84 are also sized to receive one of two coated wires of the electrical conduit 20, each wire of which extends through one of the spacers 84 as best seen in FIG. 7. Maintaining the water seal of the interior of the device 12 is again established by O-rings 74 at each end of each of these spacers 84.

Positioned within the motor module cap 62 are two electrical contacts 68 and 70 which are longitudinally floatingly positioned for biased axial movement in the direction of arrow C by compression springs 76. The contact blocks 68 and 70 are supported within slots formed into non-conductive arcuately configured spacers 82 which are themselves held in position by threaded fasteners as best seen in FIG. 4. The distal end portions of the electrical conduit 20 are preferably stripped of insulation to expose the conductive interior wiring and then clamped into position within mating holes formed through each of the contact blocks 58 by set screws 92. By this arrangement, when the motor module cap 62 is locked into place as previously described, electrical contact between contact blocks 68 and 70 is automatically made with the motor contacts 56 and 58, respectively. Again, note that alignment pin 94 in FIG. 7 establishes proper rotational alignment and immobilization rotationally between the motor 48 and the inner housing 46.

The outlet port 90, as seen in FIG. 7, is formed axially through the outlet cap 72 which threadably receives a conduit nipple 26 shown in FIG. 4 for receiving the lower end of the flexible conduit 22 as shown in FIG. 1. By this arrangement the groundwater flowing into the device in the direction of arrow A through inlet ports 44 flows upwardly through the passageway 88 for discharge upward through outlet port 90.

Note that the water flow through water passage 88 cools the motor 48 for increasing motor life and efficiency.

Figure 8:
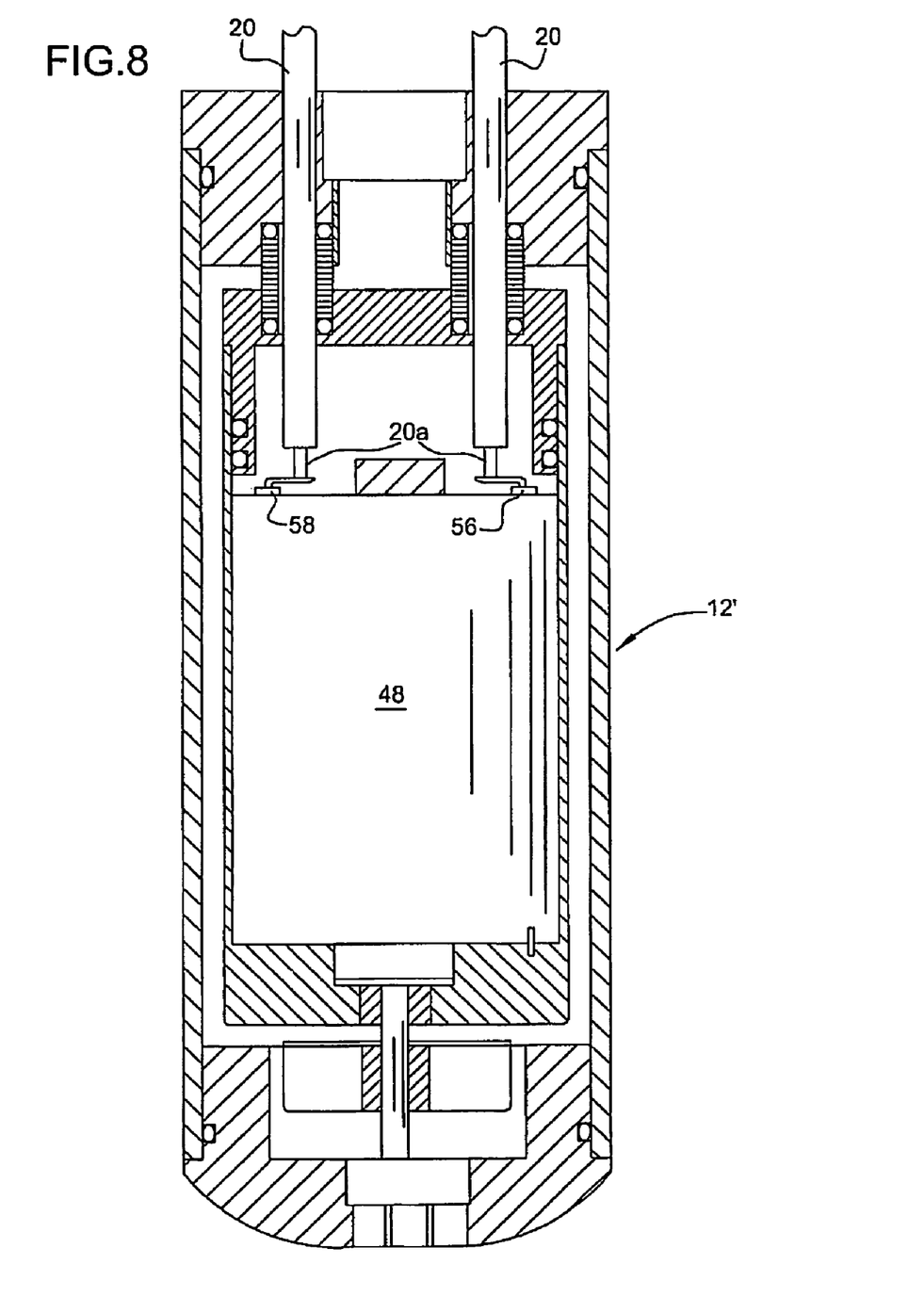
FIG. 8 is an alternate embodiment of FIG. 7.

Referring now to FIG. 8, an alternate embodiment of the sampling device is there shown generally at numeral 12' and includes all of the same components previously shown in FIG. 7 except as noted herebelow. However, in this embodiment, the lower distal ends of the electrical conduit 20, which are stripped of their insulated coatings, are soldered or mechanically attached at 20a to the electrical contacts 56 and 58 of the motor 48.

In either case, simple replacement of the motor 48 is easily accomplished when required. This motor replacement procedure, as best understood from FIGS. 4 to 7, after removal of the water impeller 50, involves unscrewing a sub-assembly of (a) the inner housing 46 with motor 48 therein (b) the motor module 62 connected to (c) the output cap 72. The inner housing 46 with motor 48 therein is then twisted and pulled free of the motor module cap 62/output cap 72. Thereafter, the motor 48 is slidably removed from the inner housing 46 by applying axial pressure against the end of the output shaft 52. This procedure is reversed to install a new motor.

Figure 9:
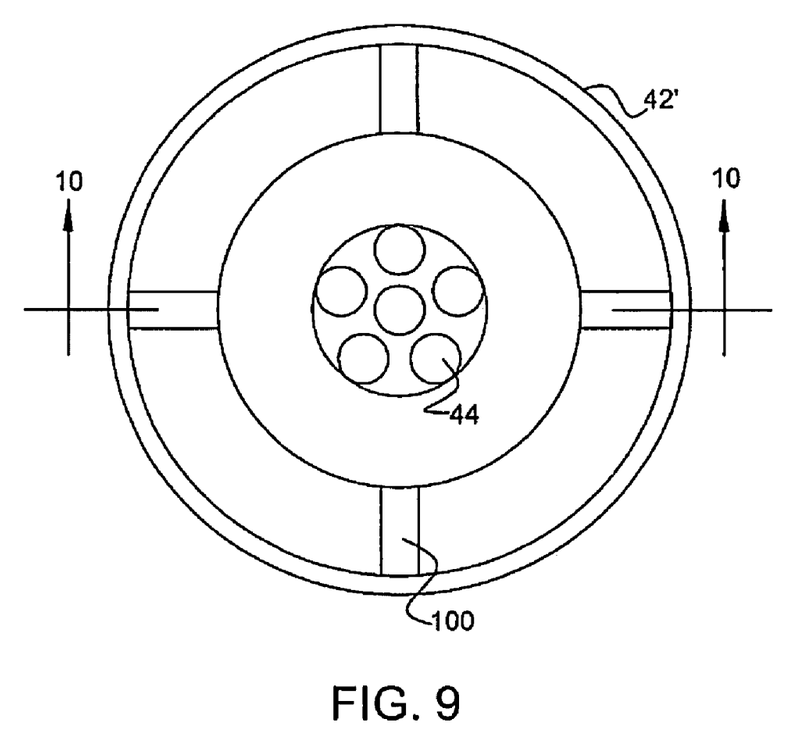
FIGS. 9 and 10 are alternate embodiments of the bottom of the outer housing of FIGS. 7 and 8.
Figure 10:
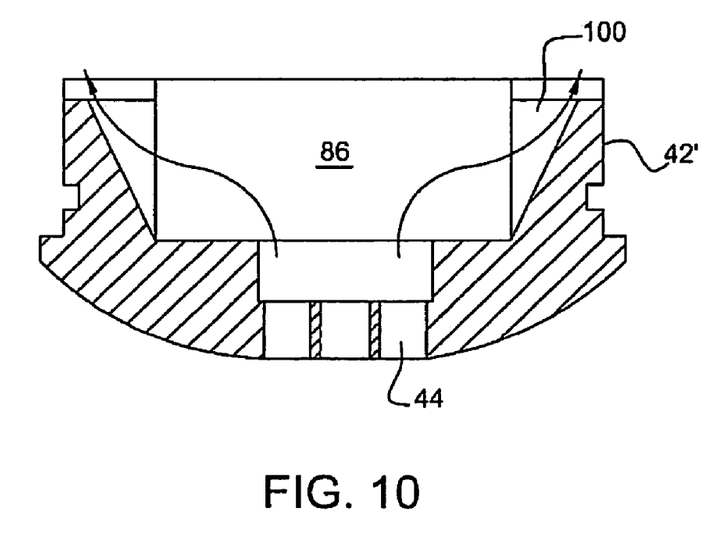

Referring lastly to FIGS. 9 and 10, an alternate preferred embodiment of the bottom member 42' of the outer housing is there shown. In this embodiment, which is also formed of machined stainless steel, the inlet ports 44 extend into radially spaced diagonally upwardly opening slots 100 which have been shown to greatly increase head pressure and thusly the overall flow at any specified submerged depth of the device 12'. The smooth flow of the groundwater shown by the arrows in FIG. 10 is presumed to be the source of this operational benefit.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

The invention claimed is:

1. A replaceable internal electric motor for a groundwater sampling device for withdrawing groundwater from a well comprising:

a DC-operated electric motor positionable within said groundwater sampling device, said motor comprising an output shaft capable of downwardly extending through a sealed hole in an inner housing of the groundwater sampling device;

means on said motor to align said motor with an alignment pin of the groundwater sampling device; and an inner housing slidably, then twistably lockable to a motor module cap by mating engagement of a plurality of uniquely spaced L-shaped slots formed into the upper end of said inner housing and an equal plurality Of pins extending radially outwardly from said motor module cap.

2. The motor claim 1, wherein said motor further comprises an aperture of a size and shape to align with an alignment pin.

3. The motor of claim 1, operating between 12.6 and 17.4 VDC.

4. The motor of claim 1 further comprises a seal for said output shaft.

5. The motor of claim 1, further comprising an impeller coupled to the output shaft.

6. The motor of claim 5, wherein the motor, the output shaft and the impeller are removable as one unit.

7. A replaceable internal electric motor for a groundwater sampling device for withdrawing groundwater from a well comprising:
- a DC-operated electric motor positioned within said groundwater sampling device, said motor comprising an upper end having electrical input terminals; and a motor module cap having electrical output terminals coupleable to said ground water sampling device, wherein said cap makes automatic biased contact with the electrical input terminals of said motor upon assembly of the device, wherein said motor module cap is rotatably couplable by mating engagement of a plurality of spaced L-shaped slots formed into the upper end of an inner housing and an equal plurality of pins extending radially outwardly from said motor module cap.

8. The motor of claim 7, operating between 12.6 and 17.4 VDC.

9. The motor of claim 7 further comprising an output shaft and alignment means on the same side of the motor as said output shaft to prevent the motor from turning within a groundwater sampling device.

10. A replaceable internal electric motor for a groundwater sampling device for withdrawing groundwater from a well comprising:
- a DC-operated electric motor positionable within said groundwater sampling device, said motor comprising an output shaft capable of downwardly extending through a sealed hole in an inner housing of the groundwater sampling device;
- means on said motor to align said motor with an alignment pin of the groundwater sampling device; and an inner housing slidably, then twistably lockable to a motor module cap by mating engagement of at least one L-shaped slot formed into the upper end of said inner housing and at least one pin extending radially outwardly from said motor module cap.

11. A replaceable internal electric motor for a groundwater sampling device for withdrawing groundwater from a well comprising:
- a DC-operated electric motor positioned within said groundwater sampling device, said motor comprising an upper end having electrical input terminals; and a motor module cap having electrical output terminals coupleable to said ground water sampling device, wherein said cap makes automatic biased contact with the electrical input terminals of said motor upon assembly of the device, wherein said motor module cap is rotatably couplable by mating engagement of at least one L-shaped slot formed into the upper end of an inner housing and at least one pin extending radially outwardly from said motor module cap.

\* \* \* \* \*